(12) United States Patent
Saur et al.

(10) Patent No.: US 12,023,208 B2
(45) Date of Patent: Jul. 2, 2024

(54) METHOD FOR OPERATING A VISUALIZATION SYSTEM IN A SURGICAL APPLICATION, AND VISUALIZATION SYSTEM FOR A SURGICAL APPLICATION

(71) Applicant: Carl Zeiss Meditec AG, Jena (DE)

(72) Inventors: Stefan Saur, Aalen (DE); Christoph Hauger, Aalen (DE); Christoph Schaeff, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 17/529,049

(22) Filed: Nov. 17, 2021

(65) Prior Publication Data
US 2022/0175485 A1    Jun. 9, 2022

(30) Foreign Application Priority Data
Dec. 9, 2020   (DE) ............... 10 2020 215 559.3

(51) Int. Cl.
*A61B 90/00*   (2016.01)
*A61B 34/20*   (2016.01)
*G06T 19/00*   (2011.01)

(52) U.S. Cl.
CPC .............. *A61B 90/36* (2016.02); *A61B 34/20* (2016.02); *G06T 19/006* (2013.01); *A61B 2034/2055* (2016.02); *A61B 2090/365* (2016.02)

(58) Field of Classification Search
CPC ........ G06T 19/006; A61B 90/36; A61B 34/20
USPC ....................................................... 345/633
See application file for complete search history.

(56) References Cited

U.S. PATENT DOCUMENTS

| 9,911,214 | B2 * | 3/2018 | Zhou | G06F 3/14 |
| 11,273,003 | B1 * | 3/2022 | Haider | G02B 27/0093 |
| 2008/0024597 | A1 * | 1/2008 | Yang | H04N 13/344 |
| | | | | 348/E13.001 |

(Continued)

FOREIGN PATENT DOCUMENTS

WO    WO 2015/149557 A1    10/2015

*Primary Examiner* — Javid A Amini
(74) *Attorney, Agent, or Firm* — NIXON PEABODY LLP; Jeffrey L. Costellia (57) ABSTRACT

The invention relates to a method for operating a visualization system in a surgical application, wherein at least one image representation of a region to be operated on and/or operated on is captured by means of a capturing device, wherein the at least one image representation is displayed on a main display device, wherein a pose of a visualization device that can be worn on the head relative to a display surface of the main display device is captured by means of a pose sensor system, and wherein at least one three-dimensional augmentation information item corresponding to the at least one image representation displayed is generated and/or provided and is displayed on a display device of the visualization device, wherein the augmentation information item is generated and/or provided in consideration of the captured pose in such a way that the at least one image representation displayed on the main display device is extended into a three-dimensional region by the at least one three-dimensional augmentation information item corresponding to said at least one image representation. Furthermore, the invention relates to a visualization system for a surgical application.

9 Claims, 4 Drawing Sheets

(56) References Cited

U.S. PATENT DOCUMENTS

| | | | |
|---|---|---|---|
| 2013/0033485 A1* | 2/2013 | Kollin | G06F 3/0484 |
| | | | 345/660 |
| 2017/0076475 A1* | 3/2017 | Zhou | G06F 3/14 |
| 2017/0258526 A1* | 9/2017 | Lang | H05K 999/99 |
| 2019/0250873 A1* | 8/2019 | Blume | G16H 20/40 |
| 2022/0179359 A1* | 6/2022 | Pi | G03H 1/2294 |

* cited by examiner

METHOD FOR OPERATING A VISUALIZATION SYSTEM IN A SURGICAL APPLICATION, AND VISUALIZATION SYSTEM FOR A SURGICAL APPLICATION

CROSS-REFERENCE TO RELATED APPLICATIONS

This application claims foreign priority under 35 U.S.C. § 119 to and the benefit of German Patent Application No. 10 2020 215 559.3, filed on Dec. 9, 2020, which is incorporated herein by reference in its entirety.

FIELD OF THE INVENTION

The invention relates to a method for operating a visualization system in a surgical application, and to a visualization system for a surgical application.

BACKGROUND

In the context of carrying out medical interventions, particularly in (micro)surgery, use is increasingly being made of technical aids, such as large-area display devices, which enable additional items of information to be displayed. This can involve for example displaying a video data stream of a surgical site in real time, said video data stream being captured by means of a capturing device, in particular by means of a surgical microscope equipped with a camera. In the case of an operation carried out exoscopically with the aid of such a (possibly robotic) visualization system, the display device is a large screen installed in the operating room.

WO 2015/149557 A1 discloses a display control method and a display control device which relate to the field of near-to-eye display technologies. The method comprises: determining a first display area, in the field of view of a user, of an image displayed on a main display device; and using at least one near-to-eye display device according to the first display area to display augmentation information related to the image. In the method and the device, at least one near-to-eye display device is used to supplement a display that is provided at a suitable viewing distance of a user by a device but cannot fully fill the field of view of the user, and augmentation information is used to fill the field of view of the user as far as possible in order that a good experience can be obtained when viewing immersion media.

SUMMARY OF THE INVENTION

The problem addressed by the invention is that of providing a method for operating a visualization system in a surgical application and a visualization system for a surgical application which can improve a user's workflow.

According to the invention, the problem is solved by a method having the features of patent claim 1 and a visualization system having the features of patent claim 10. Advantageous configurations of the invention are evident from the dependent claims.

One of the basic concepts of the invention is to augment an image representation captured from a region to be operated on and/or operated on with the aid of at least one three-dimensional augmentation information item. As a result, a surgeon or an assisting person can be provided with additional items of information which can support a medical operation particularly with regard to a spatial orientation and a workflow. For this purpose, the at least one three-dimensional augmentation information item is displayed to a user, in particular to a surgeon, on a display device of a visualization device that can be worn on the head. In order to display the at least one augmentation information item in a suitable manner, a pose of the visualization device relative to a display surface of a main display device, on which at least one captured image representation of the region to be operated on and/or operated on is displayed, is captured by means of a pose sensor system. The at least one three-dimensional augmentation information item is generated and/or provided in consideration of the captured pose, specifically in such a way that the at least one image representation displayed on the main display device is extended into a three-dimensional region by the at least one three-dimensional augmentation information item. To put it another way, the generating and/or providing are/is effected in particular in such a way that the at least one three-dimensional augmentation information item, for a user of the visualization device, appears in a three-dimensional region around the display surface of the main display device in a manner corresponding to the at least one image representation displayed. Since the at least one three-dimensional augmentation information item is generated and/or provided (and displayed) in a manner corresponding to the at least one image representation displayed, the at least one image representation and the at least one three-dimensional augmentation information item are perceived by the user of the visualization device as uniform and interrelated in terms of contents and/or contextually. In particular, a transition between the contents is positionally accurate and true to scale in this case, and so in particular a smooth transition can be captured.

In particular, a method for operating a visualization system in a surgical application is provided, wherein at least one image representation of a region to be operated on and/or operated on is captured by means of a capturing device of the visualization system, wherein the at least one image representation is displayed on a main display device, wherein a pose of a visualization device that can be worn on the head relative to a display surface of the main display device is captured by means of a pose sensor system, and wherein at least one three-dimensional augmentation information item corresponding to the at least one image representation displayed is generated and/or provided and is displayed on a display device of the visualization device that can be worn on the head, wherein the at least one three-dimensional augmentation information item is generated and/or provided in consideration of the captured pose in such a way that the at least one image representation displayed on the main display device is extended into a three-dimensional region by the at least one three-dimensional augmentation information item corresponding to said at least one image representation.

Furthermore, in particular, a visualization system for a surgical application is provided, comprising a capturing device, configured for capturing at least one image representation of a region to be operated on and/or operated on, a main display device, configured for displaying the at least one image representation captured, a visualization device that can be worn on the head with a display device, a pose sensor system, configured for capturing a pose of the visualization device that can be worn on the head relative to a display surface of the main display device, and a control device, wherein the control device is configured to generate and/or to provide at least one three-dimensional augmentation information item corresponding to the at least one image representation displayed and to communicate it for display to the display device of the visualization device that can be worn on the head, and to carry out the generating and/or providing of the at least one three-dimensional augmentation information item in consideration of the captured pose in such a way that the at least one image representation displayed on the main display device is extended into a three-dimensional region by the at least one three-dimensional augmentation information item corresponding to said at least one image representation.

One advantage of the method and of the visualization system is that the at least one three-dimensional augmentation information item can be registered by a user of the visualization device that can be worn on the head in particular in interaction in terms of contents and in spatial interaction with the at least one image representation displayed on the display surface of the main display device. This makes it possible to provide the user with a wide range of three-dimensional additional information during an operation. This additional information provided by way of the at least one augmentation information item can be arranged in terms of contents and locally (in particular spatially) during display in each case on, in front of or behind the at least one image representation displayed. This makes it possible in particular, during display, to use all three dimensions and in particular to provide the three-dimensional location information as additional information, such that an information flow to the user and a workflow during a surgical procedure can be improved.

A main display device is in particular a screen, a television set, a monitor and/or some other display device arranged in a stationary fashion. The main display device is arranged in particular in an operating room, such that a surgeon and/or an assisting person can register it without further aids.

The visualization system is in particular a visualization system that serves for visualization during medical, in particular surgical or microsurgical, operations. The visualization system can be for example an operation system, in particular a (robotic) surgical operation microscope. Alternatively, a surgical operation system, in particular an operation microscope, can also comprise the visualization system. The visualization system comprises a capturing device. The capturing device is in particular a camera which captures a capture region, in particular a region to be operated on and/or operated on, with a first image size (e.g. 4K) and provides at least one image representation, in particular a video data stream. The capturing device, in particular the camera, can comprise an optical imaging device enabling a magnification and a focus to be set. The visualization system can furthermore comprise an actuator system enabling at least one pose, in particular a position and/or an orientation, of the capturing device to be altered, such that a position of a capture region of the capturing device can be altered by this means. The visualization system may then also be referred to as a robotic visualization system. The actuator system can be embodied in particular as a robotic stand of the capturing device. The visualization system furthermore comprises a control device, a pose sensor system and a visualization device that can be worn on the head. The control device and the visualization device are connected to one another via a wired or wireless communication connection. The visualization device comprises a display device, on which the at least one three-dimensional augmentation information item is displayed, such that a user can register the latter.

The pose sensor system is arranged in particular on the visualization device that can be worn on the head, or can be part of the visualization device. Alternatively or additionally, the pose sensor system can also be arranged elsewhere. By way of example, provision can be made for the pose sensor system alternatively or additionally to be arranged at a suitable position in a room in which the visualization system is used.

The pose of the visualization device that can be worn on the head is captured by means of the pose sensor system. In this case, a pose comprises in particular a position and an orientation of the visualization device or alternatively or additionally a pose of the head of the user of the visualization device relative to a display surface of the main display device. On the basis of the determined pose, it is possible to determine in particular the distance between the visualization device and the display surface of the main display device and the orientation of the visualization device relative to the display surface. Provision can be made for determining the pose with reference to a (global) coordinate system of the environment. If a position and an orientation of the display surface of the main display device within said (global) coordinate system are known, then the pose of the visualization device relative to the display surface of the main display device can be determined therefrom. The position and the orientation of the display surface of the main display device can likewise be determined by means of the pose sensor system or alternatively can be predefined or have been predefined fixed.

Provision can be made for the pose of the visualization device to be captured or determined by means of inside out tracking, wherein for this purpose the pose sensor system comprises an environment sensor system arranged in particular on the visualization device. A three-dimensional, geometric spatial model of the environment can be created by means of the environment sensor system, in particular by means of a camera and/or depth sensors. This is done for example by means of the simultaneous localization and mapping (SLAM) method, known per se. By means of the spatial model and inertial measurement units (IMUs) of the pose sensor system, it is then possible to determine the pose of the visualization device in the environment and/or relative to the display surface of the main display device. Provision can be made for identifying the display surface of the main display device for capturing the pose with the aid of methods of computer vision and/or of machine learning. This can be done with or without the aid of markings additionally arranged on the display surface.

The visualization device that can be worn on the head is embodied in particular as a head-mounted display (HMD). The visualization device can comprise a screen, for example, by means of which an environment can be captured directly and on which an additional content can be projected, which can be registered by the user together and/or in superimposition with the real environment. The screen in interaction with the projection forms in particular the display device of the visualization device. The visualization device can comprise the pose sensor system or a part of the pose sensor system. By means of the visualization device, it is possible, in particular, additionally or alternatively to represent further items of information on the display device besides a real environment and the at least one augmentation information item. The visualization device can comprise further devices, for example a control device for controlling the display device, the pose sensor system and further devices, insofar as these are present. Furthermore, the visualization device can also comprise the control device of the visualization system. The visualization device can be battery-operated or fed via an external power supply. The visualization device can be configured to provide augmented reality (AR), mixed reality (MR) and/or virtual reality (VR). The visualization device that can be worn on the head may in particular also be referred to as AR glasses.

Provision is made, in particular, for the method to be repeated cyclically. As a result, a current at least one three-dimensional augmentation information item can be continuously generated and/or provided and displayed in consideration of a current pose of the visualization device.

Parts of the visualization system, in particular the control device, can be embodied individually or jointly as a combination of hardware and software, for example as program code that is executed on a microcontroller or microprocessor. However, provision can also be made for parts to be embodied individually or jointly as an application-specific integrated circuit (ASIC). In particular, the control device comprises a computing device and a storage device (main memory and/or long-term storage facility) and in particular suitable interfaces for forming communication connections to the capturing device, the main display device, the pose sensor system and the visualization device that can be worn on the head and also further devices, insofar as these are present.

In one embodiment it is provided that a pose of the capturing device relative to the region to be operated on and/or operated on is determined, wherein the at least one three-dimensional augmentation information item is generated and/or provided in consideration of the determined pose of the capturing device. As a result, the at least one augmentation information item can be generated and/or provided in a manner corresponding to the region to be operated on and/or operated on which is imaged in the at least one captured image representation. In this case, in a manner corresponding to one another is intended to mean, in particular, that the at least one augmentation information item displayed is positionally accurate and true to scale with regard to a size and a position relative to the at least one image representation displayed on the display surface of the main display device. If the at least one augmentation information item comprises for example preoperative tumor segmentations or fiber tracts of the brain or a vascular structure, then these can be generated and/or provided and displayed positionally accurately and true to scale given a known pose of the capturing device relative to the region to be operated on and/or operated on. Provision can be made for capturing and/or determining the pose of the capturing device for example in a coordinate system relative to the patient. On the basis of the pose of the capturing device determined in said coordinate system, a capture region can be determined, wherein a magnification etc. of the capturing device can also be taken into account in this case. Once the capture region has been determined, then the at least one augmentation information item can be determined in terms of contents, for example by having recourse to, in particular three-dimensional, measurement data of medical measuring instruments. In this case, in particular, a portion of the measurement data is determined which corresponds to the capture region determined and which accordingly is intended to be generated and/or provided and displayed as augmentation information.

In one embodiment it is provided that a topography of the region to be operated on and/or operated on is captured and/or received, wherein the at least one three-dimensional augmentation information item is generated and/or provided in consideration of the captured and/or received topography. As a result, a user can be provided with topographic information of the region to be operated on and/or operated on in superimposition with the at least one image representation. The topography can be captured and provided by means of stereoscopy, for example, wherein the region to be operated on and/or operated on is captured stereoscopically and associated stereoscopic data are arranged in a coordinate system, for example in a coordinate system with reference to the patient which corresponds to the at least one image representation captured. On the basis of this, the at least one augmentation information item is generated and/or provided by means of the control device. The topographic data or the topography are or is then displayed three-dimensionally on the display device of the visualization device, such that the user can register same positionally accurately and true to scale in superimposition with the at least one image representation.

In one embodiment it is provided that three-dimensional tomographic data corresponding to the region to be operated on and/or operated on are captured and/or received, wherein the at least one three-dimensional augmentation information item is generated and/or provided in consideration of the captured and/or received three-dimensional tomographic data. As a result, items of information concerning internal regions of organs or tissue can also be provided in superimposition with the at least one image representation. By way of example, a tumor can be displayed three-dimensionally in superimposition with the at least one image representation in order to display the outer contour and/or a segmentation of the tumor to a surgeon during preparatory work concerning the tumor and/or during removal of tumor tissue. The procedure is in principle analogous to that in the embodiment described above. In particular, provision is made for the tomographic data to be present in a coordinate system in which a position and orientation of the at least one image representation captured are also known. Tomographic data can comprise for example a tumor segmentation, fiber tracts in the brain and/or a vascular structure. The tomographic data are based on captured measurement data, in particular. However, alternatively or additionally, provision can also be made for the tomographic measurement data to comprise modeled and/or simulated data, for example a modeled and/or simulated vascular structure, etc. For capturing and/or providing the tomographic data, methods and apparatuses known per se can be used, for example computed tomography, magnetic resonance imaging or optical coherence tomography.

In one embodiment it is provided that with reference to the at least one image representation displayed and/or the captured and/or received topography and/or the captured and/or received tomographic data at least one three-dimensional marking is generated and/or received, wherein the at least one three-dimensional augmentation information item is generated and/or provided in consideration of the at least one three-dimensional marking. As a result, points and/or regions can be provided with markings which facilitate the subsequent identification and/or finding again. To put it another way, by means of a marking a kind of bookmark can be placed which particularly highlights a position or a region of interest and facilitates an orientation and also finding again and/or a step by step procedure and/or processing. Provision can be made, for example, for a user of the visualization device, for example a surgeon, during an operative intervention, to mark specific points or regions of a tumor for later handling or diagnosis, etc. For such a marking, at least one three-dimensional position with reference to a coordinate system, for example with reference to the patient or the region to be operated on and/or operated on, is then defined and stored, for example in a memory of the control device. It can be provided that content information items concerning the marking can additionally be stored and displayed, for example a color, a text, dimensions, a texture and/or a pattern, etc. These can then likewise be taken into account when generating and providing the at least one augmentation information item.

In one embodiment it is provided that a pose of at least one actuation element is captured, wherein the at least one three-dimensional augmentation information item is generated and/or provided in consideration of the captured pose of the at least one actuation element. As a result, a pose, in particular a three-dimensional position and/or orientation, of the at least one actuation element in relation to the at least one image representation or in relation to the region to be operated on and/or operated on can be clarified by a corresponding augmentation information item being generated and/or provided. An actuation element is user-controlled, in particular. An actuation element can be for example a hand of a surgeon or of an assisting person or a surgical tool or aid. In particular, this can facilitate for a surgeon or an assisting person an orientation in relation to the at least one image representation displayed. A workflow can be improved as a result. The pose of the at least one actuation element can be captured and provided by means of a stereoscopic method, for example. Alternatively or additionally, the pose of the at least one actuation element can also be determined or estimated by means of methods of computer vision and/or of machine learning, for example by means of an object tracking method in which the at least one aid is identified in a captured image representation and a pose of the at least one aid is estimated on the basis thereof. By way of example, at a three-dimensional position estimated in the context of pose estimation, a graphical symbol can be displayed in order to clarify to the surgeon the three-dimensional position at which the actuation element is currently situated in relation to the region to be operated on and/or operated on.

In a developing embodiment it is provided that a trajectory is generated from the captured pose of the at least one actuation element, wherein the at least one three-dimensional augmentation information item is generated and/or provided in consideration of the generated trajectory. As a result, a distance covered or a history of the at least one actuation element can be clarified by means of the at least one augmentation information item. An orientation of the user in relation to the region to be operated on and/or operated on is supported and improved even further as a result. In particular, the captured poses are linked with one another and stored, for example in a memory of the control device.

In one embodiment it is provided that additionally at least one two-dimensional augmentation information item is generated and/or provided, wherein the at least one two-dimensional augmentation information item is displayed by means of the display device of the visualization device that can be worn on the head in such a way that said information is at least partly superimposed on the display surface of the main display device and/or that said information extends the display surface of the main display device. As a result, two-dimensional information items, for example information items superimposed directly into a plane of the display surface, can also be generated and provided. Furthermore, as a result, the display surface of the main display device can be extended two-dimensionally, such that for example a region around the edge of the display surface can be enriched with additional items of information by corresponding augmentation information items being generated and/or provided and displayed.

In one embodiment it is provided that a pose of at least one further visualization device that can be worn on the head relative to the display surface of the main display device is captured by means of the pose sensor system and/or a further pose sensor system, and wherein at least one further three-dimensional augmentation information item corresponding to the at least one image representation displayed is generated and/or provided and is displayed on a further display device of the at least one further visualization device that can be worn on the head, wherein the at least one further three-dimensional augmentation information item is generated and/or provided in consideration of the captured pose of the at least one further visualization device that can be worn on the head in such a way that the at least one image representation displayed on the main display device is extended into a three-dimensional region by the at least one further three-dimensional augmentation information item corresponding to said at least one image representation. As a result, it is possible to provide augmentation information items for a plurality of users. In particular, in this case provision can be made for mutually different augmentation information items to be provided and displayed to the users. This makes it possible to provide each user with the respectively user-specifically relevant additional information items. In this regard, for example, provision can be made for a surgeon in training or an assisting person to be provided with more and/or different augmentation information items than an experienced surgeon. The generating and/or providing of the respective augmentation information items for the plurality of users can be controlled for example by selecting user profiles stored in a memory of the control device. Said user profiles define in each case which augmentation information items are intended to be provided to the respective user.

Further features concerning the configuration of the visualization system are evident from the description of configurations of the method. The advantages of the visualization system here are in each case the same as for the configurations of the method.

BRIEF DESCRIPTION OF THE DRAWINGS

The invention is explained in greater detail below on the basis of preferred exemplary embodiments with reference to the figures. In the figures.

DETAILED DESCRIPTION

Figure 1:
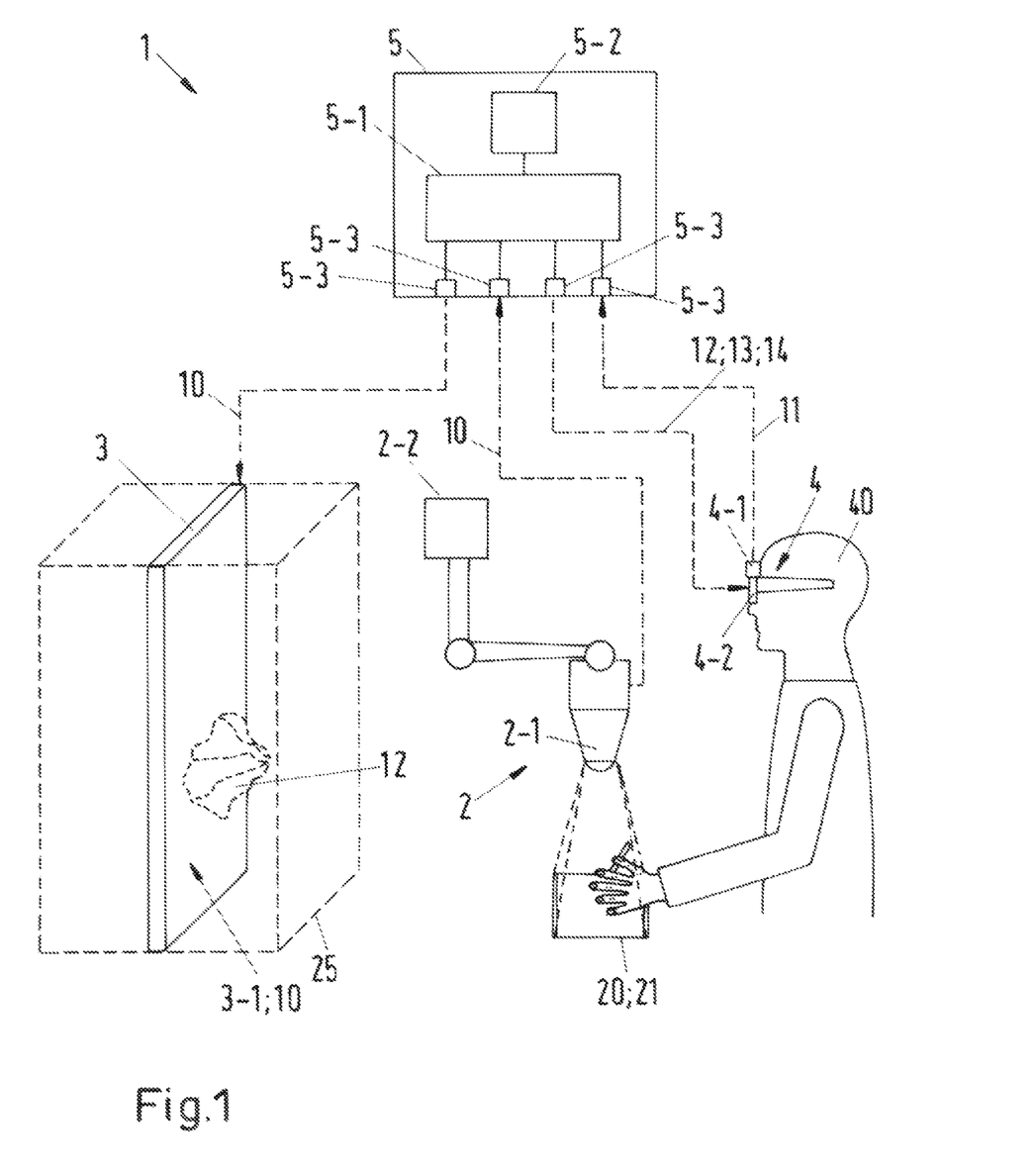
FIG. 1 shows a schematic illustration of one embodiment of the visualization system for a surgical application.

FIG. 1 shows a schematic illustration of one embodiment of the visualization system 1 for a surgical application. The visualization system 1 is used in particular in the context of an operation on a patient in an operating room. In this case, an environment of the visualization system 1 corresponds in particular to a typical environment in an operating room. The visualization system 1 comprises a capturing device 2, a main display device 3, a visualization device 4 that can be worn on the head, a pose sensor system 4-1 and a control device 5. The method for operating a visualization system in a surgical application is explained below on the basis of the visualization system 1.

The capturing device 2 comprises for example a camera 2-1 with a capture region 20, by way of which a region 21 to be operated on and/or operated on can be captured (a patient is not illustrated for the sake of clarity). The camera 2-1 is connected for example to an actuator system 2-2 via a stand, such that a pose of the camera 2-1 can be altered by means of the actuator system 2-2 in order to alter the capture region 20. The capturing device 2 can furthermore comprise an optical imaging system (not shown) enabling a focus and an image magnification of the camera 2-1 to be set. The capturing device 2 can be part of a (robotic) surgical microscope, in particular. By means of the capturing device 2, at least one image representation 10 of the region 21 to be operated on and/or operated on is captured and communicated to the control device 5, for example as image representation signal or image representation data.

The main display device 3 is for example a computer monitor or a television set (e.g. with a screen diagonal of 55"). The main display device 3 has a display surface 3-1, on which an image content can be displayed. The main display device 3 can be part of a (robotic) surgical microscope, in particular. The at least one image representation 10 captured is fed to the main display device 3 by the control device 5, wherein the at least one image representation 10 captured is displayed on the display surface 3-1.

The visualization device 4 that can be worn on the head comprises the pose sensor system 4-1 and a display device 4-2. The visualization device 4 can be for example a head-mounted display (HMD), for example AR glasses. By virtue of the visualization device 4, a user 40, in particular a surgeon or a person assisting in the operation, can perceive both the environment and a content displayed on the display device 4-2. The display device 4-2 is a three-dimensional display device, that is to say that a dedicated content can be displayed to each eye of a user 40.

The pose sensor system 4-2 is configured to capture and/or to determine a pose 11 of the visualization device 4 that can be worn on the head relative to the display surface 3-1 of the main display device 3. The pose 11 comprises a position and an orientation of the visualization device 4 relative to the display surface 3-1 of the main display device 3. The pose 11 is captured and/or determined by means of inside out tracking, for example, wherein for this purpose the pose sensor system 4-1 comprises an environment sensor system (not shown) arranged in particular on the visualization device 4. A three-dimensional, geometric spatial model of the environment can be created by means of the environment sensor system, in particular by means of a camera and/or depth sensors. This is done for example by means of the simultaneous localization and mapping (SLAM) method, known per se. By means of the spatial model and inertial measurement units (IMUs) of the pose sensor system 4-1, it is then possible to determine the pose 11 of the visualization device 4 in the environment and relative to the display surface 3-1 of the main display device 3. Provision can be made for identifying the display surface 3-1 of the main display device 3 for capturing the pose 11 with the aid of methods of computer vision and/or of machine learning. This can be done with or without the aid of markings (not shown) additionally arranged on the display surface 3-1. The captured and/or determined pose 11 is communicated to the control device 5, for example as pose signal or pose data.

Alternatively or additionally, provision can be made for the pose sensor system 4-1 also to be arranged elsewhere, in particular at a suitable position in the room in which the visualization system 1 is used.

The control device 5 comprises a computing device 5-1 and a memory 5-2. The computing device 5-1 is configured to be able to carry out computation operations on data stored in the memory 5-2 and can thereby implement measures necessary for carrying out the method. The computing device 5-1 comprises a microprocessor, for example, which can execute a program code stored in the memory 5-2 for carrying out parts of the method described in this disclosure.

The control device 5 furthermore comprises suitable interfaces 5-3 in order to be able to communicate with the capturing device 2, the main display device 3 and the visualization device 4. The control device 5 receives the at least one image representation 10 captured and feeds the at least one image representation 10 to the display device 3.

The control device 5 is configured to generate and/or to provide at least one three-dimensional augmentation information item 12 corresponding to the at least one image representation 10 captured and displayed and to communicate it for display to the display device 4-2 of the visualization device 4 that can be worn on the head. In this case, corresponding means, in particular, that the at least one augmentation information item 12 together with the at least one image representation 10 displayed on the display surface 3-1 forms an interrelated impression in terms of contents. By way of example, the at least one three-dimensional augmentation information item 12 can supplement and/or extend a two-dimensional image content comprised by the at least one image representation 10 into the third dimension.

In this case, provision is made for the control device 5 to carry out the generating and/or providing of the at least one three-dimensional augmentation information item 12 in consideration of the captured pose 11 in such a way that the at least one image representation 10 displayed on the main display device 3 is extended into a three-dimensional region 25 by the at least one three-dimensional augmentation information item 12 corresponding to said at least one image representation. The at least one image representation 10 and the at least one three-dimensional augmentation information item 12 corresponding thereto can then be registered by the user 40 in particular jointly and in an interrelated manner. In this case, the three-dimensional region 25 illustrated in FIG. 1 has been chosen merely by way of example. The three-dimensional region 25 can be embodied either smaller or larger and can also have a different shape. For this purpose, the control device 5 receives the captured pose 11 and evaluates it. The pose 11 comprises in particular a position and an orientation of the visualization device 4 relative to the display surface 3-1 of the main display device 3. On the basis thereof and on the basis of the at least one augmentation information item 12, the control device 5 generates in particular a three-dimensional image signal 13 or three-dimensional image data 14 (e.g. side-by-side, interlaced or sequentially), which are fed to the display device 4-2, such that the at least one three-dimensional augmentation information item 12 appears to the user 40 in the three-dimensional region 25 around the display surface 3-1 in a manner corresponding to the at least one image representation 10 displayed. A three-dimensional augmentation information item 12 is shown by way of example in the three-dimensional region 25, wherein the augmentation information item 12 can be registered only by the user 40 by way of the display device 4-2 of the visualization device 4.

Provision can be made for the control device 5 to be part of the visualization device 4 that can be worn on the head. As a result, the control device 5 can be linked to the display device 4-2 with short signal propagation times, which enables communication with shortened latencies and fosters a real-time experience by the user. In particular, this also makes it possible to react in an improved way to rapid head movements of the user and an associated change in the pose of the visualization device 4.

For generating and/or providing the at least one augmentation information item 12, the control device 5 can use for example a three-dimensional model which is generated from medical data (e.g. topographic and/or tomographic data) and which is stored in the memory 5-2 of the control device 5. Depending on the captured pose of the visualization device 4 relative to the display surface 3-1 of the main display device 3, the control device 5 calculates a three-dimensional perspective view of the three-dimensional model in a manner corresponding to the at least one image representation 10 and provides this calculated view as at least one augmentation information item 12. The generating can also be effected step by step, wherein after calculating a first three-dimensional view, shortly before displaying the at least one augmentation information item 12, the three-dimensional view is once again calculated and/or updated on the basis of a currently captured pose.

Figure 2:
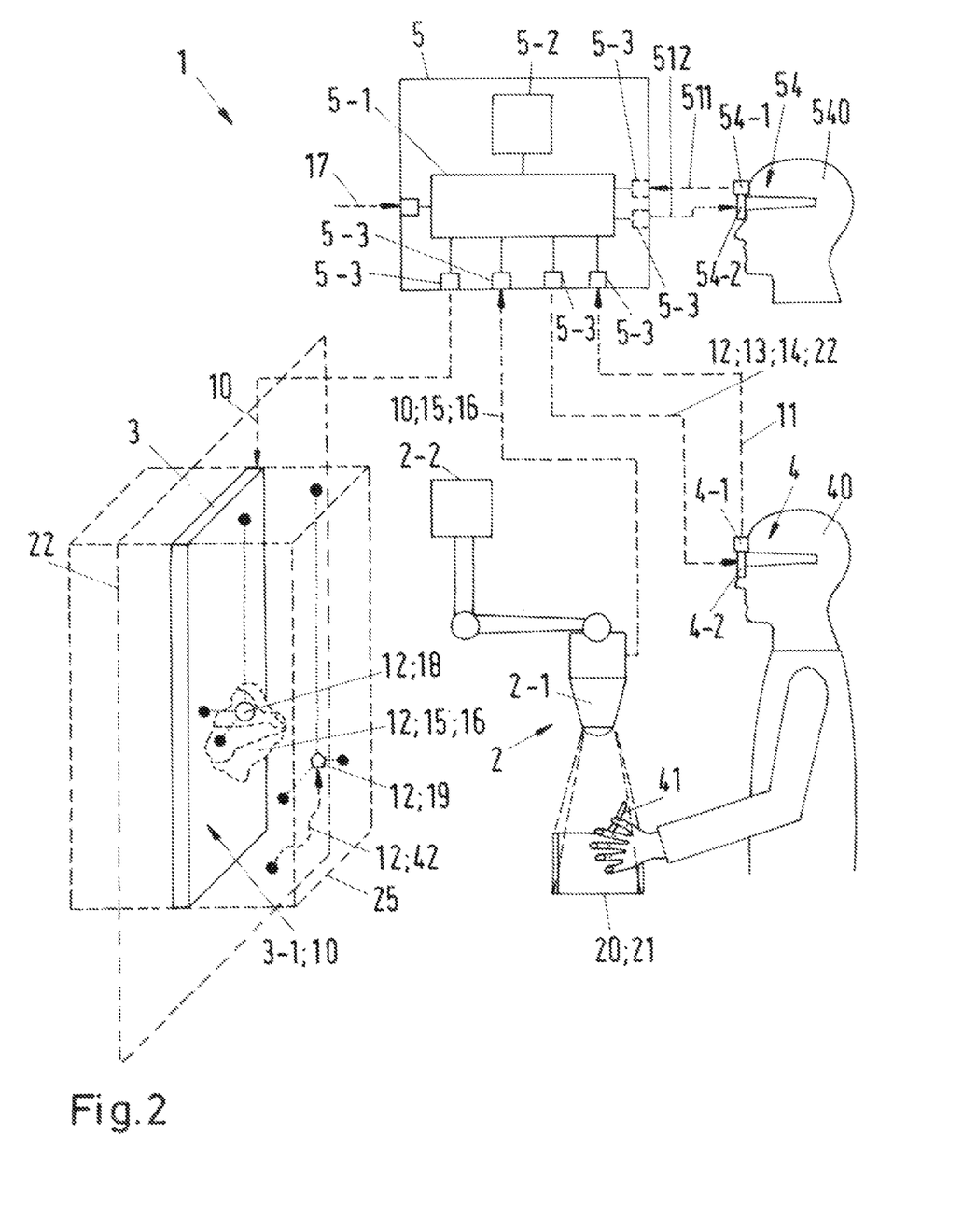
FIG. 2 shows a schematic illustration of further embodiments of the visualization system and of the method.

FIG. 2 shows a schematic illustration of further embodiments of the visualization system 1 and of the method described in this disclosure. The embodiments are configured in principle like the embodiment shown in FIG. 1. In this case, identical reference signs designate identical terms and features.

Provision can be made for determining a pose 15 of the capturing device 2, in particular of a camera 2-1 of the capturing device 2, relative to the region 21 to be operated on and/or operated on, wherein the at least one three-dimensional augmentation information item 12 is generated and/or provided by means of the control device 5 in consideration of the determined pose 15 of the capturing device 2. The pose 15 of the capturing device 2 relative to the region 21 to be operated on and/or operated on can be determined for example with the aid of methods of computer vision and/or of machine learning. Alternatively or additionally, the pose 15 of the capturing device 2 can be captured or determined by means of an optical and/or electromagnetic tracking system. As a result, it is possible to determine, in particular, what region of a patient is captured in what way (e.g. from what capturing direction with what magnification, etc.). This makes it possible to adapt the generating and/or providing of the at least one three-dimensional augmentation information item 12 to the region 21 to be operated on and/or operated on, such that a superimposition—registered by the user—of the at least one image representation 10 and the at least one three-dimensional augmentation information item 12 can be registered without deviations in relation to the respective positions, that is to say in particular positionally accurately and true to scale. It can be provided that the determined pose 15 of the capturing device 2 relative to the region 21 to be operated on and/or operated on is determined in a coordinate system with reference to a patient. This allows for example positions of examination data from imaging methods to be caused to correspond to the captured at least one image representation 10 in terms of contents and/or contextually.

It can be provided that a topography 16 of the region 21 to be operated on and/or operated on is captured and/or received, wherein the at least one three-dimensional augmentation information item 12 is generated and/or provided in consideration of the captured and/or received topography 16. In this case, in particular the determined pose 15 of the capturing device 2 can be taken into account. The topography 16 can be generated by means of stereoscopic methods, for example. In this case, provision can be made for the capturing device 2 to comprise a corresponding stereoscopically capturing device (not shown).

It can be provided that three-dimensional tomographic data 17 corresponding to the region 21 to be operated on and/or operated on are captured and/or received, wherein the at least one three-dimensional augmentation information item 12 is generated and/or provided in consideration of the captured and/or received three-dimensional tomographic data 17. In this case, in particular, the determined pose 15 of the capturing device 2 can be taken into account. In particular, it can be provided that the tomographic data 17 are captured or were captured by means of a tomographic capturing device (not shown) and are provided as a data set. The control device 5 is then configured to generate and/or provide the at least one augmentation information item 12 by means of suitable, in particular position-dependent, selection from the tomographic data 17.

It can be provided that with reference to the at least one image representation 10 displayed and/or the captured and/or received topography 16 and/or the captured and/or received tomographic data 17 at least one three-dimensional marking 18 is generated and/or received, wherein the at least one three-dimensional augmentation information item 12 is generated and/or provided in consideration of the at least one three-dimensional marking 18. The at least one three-dimensional marking 18 comprises in particular a position with reference to the region 21 to be operated on and/or operated on or the captured at least one image representation 10 and/or the display surface 3-1. An exemplary three-dimensional marking 18 is illustrated in the three-dimensional region 25. For clarifying the position of the exemplary three-dimensional marking 18, the latter is provided with auxiliary lines leading to boundary surfaces of the three-dimensional region 25. The three-dimensional marking 18 can furthermore comprise a predefined color, a predefined size or area and/or additional information, such as, for example, a symbol and/or a text. The marking 18 enables the user 40 to place path markers and/or bookmarks which can structure, simplify and support a workflow.

It can be provided that a pose 19 of at least one actuation element 41 is captured, wherein the at least one three-dimensional augmentation information item 12 is generated and/or provided in consideration of the captured pose 19 of the at least one actuation element 41. The actuation element 41 is for example a hand of the user 40 or a surgical tool guided by the user 40. The pose 19 of the at least one actuation element 41 can be determined for example with the aid of methods of computer vision and/or of machine learning on the basis of the captured at least one image representation 10, for example by means of methods of object tracking. It can be provided, for example, that the at least one augmentation information item 12 is generated and/or provided in such a way that a position in the three-dimensional region 25 is marked which coincides with the pose 19 of the actuation element 41, as indicated by way of example in FIG. 2.

In a development it can be provided that a trajectory 42 is generated from the captured pose 19 of the at least one actuation element 41, wherein the at least one three-dimensional augmentation information item 12 is generated and/or provided in consideration of the generated trajectory 42. For this purpose, captured poses 19 of the at least one actuation element 41 are linked to form a trajectory 42 by means of the control device 5.

It can be provided that additionally at least one two-dimensional augmentation information item 22 is generated and/or provided, wherein the at least one two-dimensional augmentation information item 22 is displayed by means of the display device 4-2 of the visualization device 4 that can be worn on the head in such a way that said information is at least partly superimposed on the display surface 3-1 of the main display device 3 and/or that said information extends the display surface 3-1 of the main display device 3, as is illustrated schematically in FIG. 2.

It can be provided that a pose 511 of at least one further visualization device 54 that can be worn on the head relative to the display surface 3-1 of the main display device 3 is captured by means of the pose sensor system 4-1 and/or a further pose sensor system 54-1, and wherein at least one further three-dimensional augmentation information item 512 corresponding to the at least one image representation 10 displayed is generated and/or received and is displayed on a further display device 54-2 of the at least one further visualization device 54 that can be worn on the head. The control device 5 is configured to generate and/or to provide the at least one further three-dimensional augmentation information item 512 in consideration of the captured pose 511 of the at least one further visualization device 54 that can be worn on the head in such a way that the at least one image representation 10 displayed on the main display device 3 is extended into a three-dimensional region 25 by the at least one further three-dimensional augmentation information item 512 corresponding to said at least one image representation. The at least one image representation 10 and the at least one further three-dimensional augmentation information item 512 corresponding thereto can then be registered by a further user 540 in particular jointly and in an interrelated manner. In this case, the three-dimensional augmentation information items 12, 512 for the user 40 and the user 540 can differ in terms of contents. Different additional information items can be provided as a result. The augmentation information items 12, 512 can be generated and/or provided for example depending on user profiles stored in the memory 5-2. By way of example, it can be provided that the at least one augmentation information item 512 for the user 540 does not comprise the markings 18 and the pose 19 of the at least one actuation element 41 and the trajectory 42.

Figure 3:
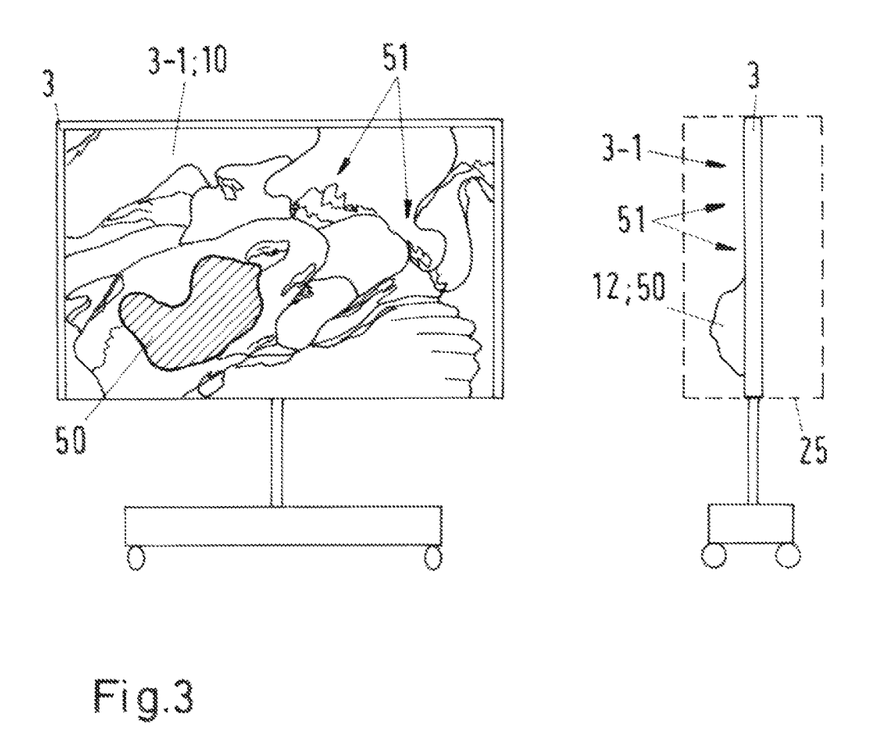
FIG. 3 shows a schematic illustration for elucidating embodiments of the visualization system and of the method.

FIG. 3 shows a schematic illustration for elucidating embodiments of the visualization system and of the method. All that is shown is the main display device 3 with the display surface 3-1, in a view from the front on the left, and in a side view on the right. The at least one image representation 10 comprises an image representation of the region to be operated on and/or operated on, said region comprising for example a tumor 50 and surrounding tissue 51. The side view illustrates a three-dimensional impression such as is registered by a user by means of the method and the visualization system described in this disclosure. The tumor 50 appears three-dimensional to the user as a result of a corresponding augmentation information item 12, whereas no such information is provided for the surrounding tissue 51 and the latter is therefore not emphasized. An orientation and a surgical procedure can be facilitated as a result.

Figure 4:
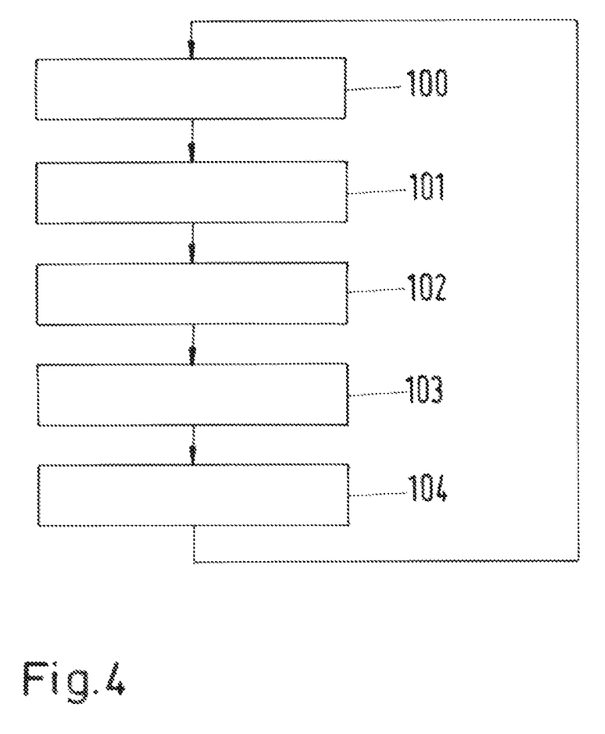
FIG. 4 shows a schematic flow diagram of one embodiment of the method for operating a visualization system in a surgical application.

FIG. 4 shows a schematic flow diagram of one embodiment of the method for operating a visualization system in a surgical application.

In a measure 100, at least one image representation of a region to be operated on and/or operated on is captured by means of a capturing device of the visualization system.

In a measure 101, the at least one image representation is displayed on a display surface of a main display device.

In a measure 102, a pose of a visualization device that can be worn on the head relative to the display surface of the main display device is captured by means of a pose sensor system.

In a measure 103, at least one three-dimensional augmentation information item corresponding to the at least one image representation displayed is generated and/or provided by means of a control device of the visualization system. In this case, the at least one three-dimensional augmentation information item is generated and/or provided in consideration of the captured pose in such a way that the at least one image representation displayed on the main display device is extended into a three-dimensional region by the at least one three-dimensional augmentation information item corresponding to said at least one image representation.

In particular, the at least one image representation and the at least one augmentation information item are considered in the same coordinate system. If necessary, the respective coordinates are generated and/or adapted to the same coordinate system by means of the control device. In this case, the coordinate system can be for example a coordinate system relative to the display surface of the main display device or a coordinate system relative to a room in which the visualization system is used. As a result of adaptation to the same coordinate system, the at least one image representation and the at least one augmentation information item are caused to correspond to one another in terms of contents and/or contextually.

In a measure 104, the at least one image representation generated and/or provided is displayed on a display device of the visualization device that can be worn on the head.

The measures 100 to 104 can be repeated. Since the pose of the visualization device on the user's head continuously changes, what is achieved as a result is that at least one augmentation information item corresponding to the current captured pose is always generated and/or provided, and it remains arranged positionally accurately and true to scale in the three-dimensional region.

LIST OF REFERENCE SIGNS

1 Visualization system
2 Capturing device
2-1 Camera
2-2 Actuator system
3 Main display device
3-1 Display surface
4 Visualization device
4-1 Pose sensor system
4-2 Display device
5 Control device
5-1 Computing device
5-2 Memory
5-3 Interface
10 Image representation
11 Pose (visualization device)
12 Augmentation information item
13 Three-dimensional image signal
14 Three-dimensional image data
15 Pose (capturing device)
16 Topography
17 Tomographic data 18 Three-dimensional marking
19 Pose (actuation element)
20 Capture region
21 Region to be operated on and/or operated on
22 Two-dimensional augmentation information item
25 Three-dimensional region
40 User
41 Actuation element
42 Trajectory
50 Tumor
51 Tissue
54 Further visualization device
54-1 Further pose sensor system
54-2 Further display device
100-104 Measures of the method
511 Pose (further visualization device)
512 Further augmentation information item
540 User

The invention claimed is:

1. A method for operating a visualization system in a surgical application, the method comprising:
   capturing at least one image representation of a region to be operated on and/or operated on by a capturing device of the visualization system;
   displaying the at least one image representation on a main display device;
   capturing a first pose by a pose sensor system, the first pose being of a visualization device worn on a head of a user relative to a display surface of the main display device;
   determining a second pose, the second pose being of the capturing device relative to the region to be operated on and/or operated on;
   generating and/or providing at least one three-dimensional augmentation information item corresponding to the at least one image representation displayed; and
   displaying the at least one three-dimensional augmentation information item on a display device of the visualization device;
   wherein the at least one three-dimensional augmentation information item is generated and/or provided in consideration of the captured first pose and the determined second pose such that the at least one image representation displayed on the main display device is extended into a three-dimensional region by the at least one three-dimensional augmentation information item corresponding to said at least one image representation.

2. The method as claimed in claim 1, the method further comprising:
   capturing and/or receiving a topography of the region to be operated on and/or operated on, wherein the at least one three-dimensional augmentation information item is generated and/or provided in consideration of the captured and/or received topography.

3. The method as claimed in claim 1, the method further comprising:
   capturing and/or receiving three-dimensional tomographic data corresponding to the region to be operated on and/or operated on,
   wherein the at least one three-dimensional augmentation information item is generated and/or provided in consideration of the captured and/or received three-dimensional tomographic data.

4. The method as claimed in claim 1, the method further comprising:
   generating and/or receiving at least one three-dimensional marking based on
   (i) the at least one image representation, and/or
   (ii) a topography of the region to be operated on and/or operated on, which is captured and/or received, and/or
   (iii) three-dimensional tomographic data corresponding to the region to be operated on and/or operated on, which is captured and/or received,
   wherein the at least one three-dimensional augmentation information item is generated and/or provided in consideration of the at least one three-dimensional marking.

5. The method as claimed in claim 1, the method further comprising:
   capturing a pose of at least one actuation element,
   wherein the at least one three-dimensional augmentation information item is generated and/or provided in consideration of the captured pose of the at least one actuation element.

6. The method as claimed in claim 5, the method further comprising:
   generating a trajectory from the captured pose of the at least one actuation element,
   wherein the at least one three-dimensional augmentation information item is generated and/or provided in consideration of the generated trajectory.

7. The method as claimed in claim 1, the method further comprising:
   generating and/or providing at least one two-dimensional augmentation information item; and
   displaying the at least one two-dimensional augmentation information item on the display device of the visualization device in such a way that said at least one two-dimensional augmentation information item is at least partly superimposed on the display surface of the main display device and/or that said at least one two-dimensional augmentation information item extends the display surface of the main display device.

8. The method as claimed in claim 1, the method further comprising:
   capturing a pose of at least one further visualization device worn on the head relative to the display surface of the main display device by the pose sensor system and/or a further pose sensor system;
   generating and/or providing at least one further three-dimensional augmentation information item corresponding to the at least one image representation displayed;
   displaying the at least one further three-dimensional augmentation information item on a further display device of the at least one further visualization device that can be worn on the head,
   wherein the at least one further three-dimensional augmentation information item is generated and/or provided in consideration of the captured pose of the at least one further visualization device such that the at least one image representation displayed on the main display device is extended into a three-dimensional region by the at least one further three-dimensional augmentation information item corresponding to said at least one image representation.

9. A visualization system for a surgical application, comprising:
   a capturing device configured to capture at least one image representation of a region to be operated on and/or operated on,
   a main display device configured to display the at least one image representation, a visualization device that can be worn on a head of a user, the visualization device including a display device, a pose sensor system configured to capture a first pose of the visualization device relative to a display surface of the main display device, and a control device, wherein the control device is configured to:

determine a second pose, the second pose being of the capturing device relative to the region to be operated on and/or operated on, generate and/or to provide at least one three-dimensional augmentation information item corresponding to the at least one image representation displayed; and communicate the at least one three-dimensional augmentation information item for display to the display device of the visualization device, wherein the at least one three-dimensional augmentation information item is generated and/or provided in consideration of the captured first pose and the determined second pose such that the at least one image representation displayed on the main display device is extended into a three-dimensional region by the at least one three-dimensional augmentation information item corresponding to said at least one image representation.

* * * * *